United States Patent [19]

Horodysky et al.

[11] 4,400,283

[45] Aug. 23, 1983

[54] MULTIFUNCTIONAL LUBRICANT ADDITIVES AND COMPOSITIONS THEREOF

[75] Inventors: Andrew G. Horodysky, Cherry Hill; Joan M. Kaminski, Mullica Hill, both of N.J.

[73] Assignee: Mobil Oil Corporation, New York, N.Y.

[21] Appl. No.: 294,590

[22] Filed: Jun. 20, 1981

[51] Int. Cl.$^3$ ............................................. C10M 1/48
[52] U.S. Cl. ............................ 252/32.7 E; 252/46.6; 252/389 A; 252/400 A; 260/399; 260/429.9; 260/429 R; 260/439 R
[58] Field of Search ............ 252/32.7 E, 46.6, 389 A, 252/400 A; 260/429 R, 439, 429.9, 399

[56] References Cited

U.S. PATENT DOCUMENTS

| | | | |
|---|---|---|---|
| 2,422,206 | 6/1947 | Musselman | 252/46.6 |
| 2,422,630 | 6/1947 | Musselman et al. | 252/32.7 E |
| 3,288,819 | 11/1966 | Tichelaar et al. | 252/32.7 E |
| 4,288,335 | 9/1981 | Rivier | 252/32.7 E |

*Primary Examiner*—Jacqueline V. Howard
*Attorney, Agent, or Firm*—Alexander J. McKillop; Michael G. Gilman; Claude E. Setliff

[57] ABSTRACT

Metal salts of partially phosphosulfurized pentaerythritol and trimethylolpropane based hydroxyl-containing esters are effective as multifunctional additives, reducing friction, inhibiting oxidation and reducing bearing corrosion when incorporated into a variety of lubricating media.

19 Claims, No Drawings

MULTIFUNCTIONAL LUBRICANT ADDITIVES AND COMPOSITIONS THEREOF

BACKGROUND OF THE INVENTION

1. Field of the Invention:

This invention is directed to multifunctional lubricant additives and to compositions containing same. A more particular aspect of this invention is directed to metal salts of partially phosphosulfurized pentaerythritol and trimethylolpropane based hydroxyl-containing esters and to lubricating fluids containing said metal salts.

2. Discussion of Prior Art:

The metal surfaces of machinery or engines operating under heavy loads wherein metal slides against metal may undergo excessive wear or corrosion. Often, the lubricants used to protect the metal surfaces deteriorate under such heavy loads and as a result, do not prevent wear at the points of metal to metal contact. Consequently, the performance of the machine or engine will suffer, and in aggravated cases the machine or engine may become completely inoperative.

It is also known that lubricants are prone to oxidative deterioration when subjected to elevated temperatures or even when they are exposed to atmospheric conditions for long periods of time. Such deterioration of lubricants, including lubricating oils and greases, produces loss of lubricating properties of the oil, grease or other lubricant subjected to oxidation.

Accordingly, there is a need for a multifunctional additive system capable of effectively reducing wear, inhibiting corrosion and reducing oxidative deterioration. There have been many attempts to devise additive systems which would provide satisfactory protection in imparting friction reducing, antioxidant and anticorrosion properties to lubricants. Many prior art additives have, however, been only marginally effective in accomplishing such objective except at unacceptably high concentrations, especially when the lubricants are subjected to drastic oxidizing conditions.

U.S. Pat. No. 3,652,410 describes multifunctional lubricant additive compositions comprising overbased metal salts and sulfur-containing compounds. U.S. Pat. No. 3,150,157 describes borated monoacylated trimethylolalkanes as motor fuel additives. However, no known art discloses or suggests the use of metal salts of pentaerythritol or trimethylolpropane based hydroxyl-containing esters as multifunctional lubricant additives.

SUMMARY OF THE INVENTION

In accordance with the present invention, it has been found that certain novel metal salts of partially phosphosulfurized polyhydric alcohol partial ester based hydroxyl-containing esters reduce friction when incorporated into lubricating fluids. These novel additives thereby reduce engine wear, inhibit oxidation and concomitantly inhibit bearing corrosion when used in, for example, internal combustion engine lubricants.

The novel compounds of this invention are metal salts of partially phosphosulfurized polyol based hydroxyl-containing esters. Zinc is the preferred metal although other metals such as nickel, iron, cobalt and molybdenum are highly useful. Lubricant compositions containing same are substantially improved with respect to antioxidant, antiwear and anticorrosion properties as well as reducing friction.

The novel additive compounds of this invention are prepared by first partially phosphosulfurizing pentaerythritol or a trimethylolalkane based hydroxyl-containing ester by reacting the hydroxyl-containing ester with a phosphosulfur compound such as phosphorus pentasulfide and (2) then reacting the partially phosphosulfurized compound, for example, partially phosphosulfurized hydroxyl-containing ester with metal compounds such as zinc oxide, zinc carbonate, zinc bicarbonate, zinc hydroxide, zinc halides such as zinc chloride and other zinc salts as well as salts of metals such as nickel, iron, cobalt, molybdenum and the like. Reaction is usually effected at a temperature between about 70° C. to about 150° C. at ambient-pressures, employing a molar ratio of the partially phosphosulfurized compound to the metal salt or other metal compound of between about 1:1 to 1:1.5.

In the first phosphosulfurization 5 to 95% of the available hydroxyl groups may be reacted with the phosphorus polysulfide. Preferably, 25-75% of the available hydroxyl groups are phosphosulfurized.

The pentaerythritol, dipentaerythritol, or trimethylolalkane (including trimethylolpropane) based hydroxyl-containing esters may be obtained commercially or prepared in any convenient manner known to the art. The synthetic ester fluids are made by an acid/alcohol reaction, selected and selectively reacted so that the product of the reaction will contain at least one free hydroxyl group (not connected with a carboxyl group). The free hydroxyl group subsequently used for phosphosulfurization will then be derived from the polyhydric alcohol. These can be made by reacting the acid and alcohol at elevated temperatures up to 260° C. or more in the presence of a catalyst such as p-toluene sulfonic acid. A solvent such as xylene or other hydrocarbon solvent can be used.

The acids useful as reactants with these alcohols include any monocarboxylic acid of the formula

where R is a straight chain, branched chain or cyclic hydrocarbyl group, or alkenyl, cycloalkyl or arylalkyl or alkylaryl group containing from about 4 to about 30 carbon atoms, or mixtures thereof, but not containing an alcoholic hydroxyl group. A particularly effective acid or mixture of acids are those having from 5 to 31 carbon atoms. Some of the acids that are suitable are valeric, hexanoic (caproic), heptanoic, octanoic, nonanoic (pelargonic), decanoic (capric), pivalic, myristic, lauric, oleic, stearic acids and the like. The acids are reacted with polyols having the general formula

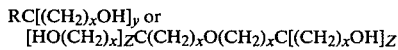

where R may be hydrogen or hydrocarbyl of up to 8 carbon atoms or $(CH_2)_xOH$, x is an integer from 1 to 4, y is 3 and Z is 3.

Among the esters particularly contemplated for use herein are mono and diesters of trimethylolpropane and the di- and triesters of pentaerythritol such as pentaerythritol trioleate, trimethylolpropane dioleate, trimethylolpropane monooleate, pentaerythritol dioleate, pentaerythritol dioleate monostearate, pentaerythritol monooleate distearate, pentaerythritol distearate, pentaerythritol tristearate, and the like. Preferably the hydroxyl-containing esters are those where one to two hydroxyl groups are available for phosphosulfurization and two ester groups are found in the molecule. The sum total of available hydroxyl groups and ester linkages must equal at least three in the reactive hydroxyl-containing ester. While not wishing to be held to a particular theory, it is believed that the most preferred phosphosulfurized product results when at least a portion of the finished additive contains at least some structures wherein an ester group, a free hydroxyl group and a phosphosulfurized hydroxyl group are present in the same molecule.

Of the various phosphorus polysulfides available, phosphorus pentasulfide is preferred.

The above-described partially phosphosulfurized pentaerythritol and trimethylolpropane based hydroxyl-containing esters may be incorporated into any suitable lubricating media such as oils of lubricating viscosity comprising mineral or synthetic oils or mixtures thereof, or greases or other solid lubricants, in which such oils may also form the base for functional fluids such as hydraulic fluids, brake fluids, power transmission fluids and the like. In general, mineral oils, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl) ether, phenoxy phenylethers, etc.

As hereinbefore indicated, the aforementioned additive compounds may also be incorporated as multifunctional agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above-described additives, are combined with a grease-forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids or forming greases can be used in preparing the aforementioned improved greases in accordance with the present invention.

It is noted that the novel additives in accordance with this invention may be used to advantage in conjunction with any known lubricant additive system. Antioxidants, antiwear agents, detergents dispersants, antifoamants, pour depressants and the like may be used in admixture with the additives of this invention without detracting from the benefits of it. Included are such additive compounds as phenates, sulfonates, methacrylates, succinimides, phosphorodithioates and the like.

DESCRIPTION OF SPECIFIC EMBODIMENTS

EXAMPLE 1

Pentaerythritol Based Hydroxyl-Containing Ester

This example illustrates the synthesis of a hydroxyl-containing ester. One mole of pentaerythritol, one and one-half moles of oleic acid and one-half mole of pelargonic acid were heated in the presence of a catalytic amount of p-toluene sulfonic acid (i.e., 0.1% of the combined weight of reactants) at a temperature of up to 240° C. Water was simultaneously removed and the reaction was continued until an acid number of less than 1 was obtained. The partial ester was filtered to yield a clear amber fluid containing 2 free hydroxyl groups.

EXAMPLE 2

Zinc Salt of Partially Phosphosulfurized Pentaerythritol Based Hydroxyl-Containing Ester Approximately 420 grams of a pentaerythritol based hydroxyl-containing ester prepared as described in Example 1 were charged to a reactor equipped with a stirrer, thermometer, condenser and a caustic scrubber. Approximately 420 grams of a hydrocarbon diluent process oil were added along with 30 grams benzene solvent. The mixture was heated to 70°–80° C. and 39 grams of phosphorus pentasulfide were added over a period of 1 hour. The reaction mixture was further held at 90° C. for 4 additional hours at which point $H_2S$ evolution diminished. The benzene solvent was removed by vacuum distillation and the partially phosphosulfurized hydroxyl-containing ester was filtered hot through paper to yield a clear amber liquid containing:

1.2% phosphorus
2.3% sulfur

Approximately 240 grams of the above partially phosphosulfurized ester was reacted with 16 grams zinc oxide in the presence of 30 grams benzene and 3 grams 2-propanol solvents for 4 hours @85°–95° C. The solvents were removed by vacuum distillation to 100° C. The product was filtered through diatomaceous earth to yield a clear amber fluid.

EXAMPLE 3

Trimethylolpropane Based Hydroxyl-Containing Ester

This example illustrates the synthesis of a hydroxyl-containing ester. One mole of trimethylolpropane, one mole of oleic acid and one-half mole of pelargonic acid were heated in the presence of a catalytic amount of p-toluene sulfonic acid at a temperature of up to 240° C. Water was simultaneously removed and the reaction was continued until an acid number of less than 1 was obtained. The partial ester was filtered to yield a clear amber fluid. The ester contained approximately 1½ free hydroxyl groups.

EXAMPLE 4

Zinc Salt of Partially Phosphosulfurized Trimethylolpropane Based Hydroxyl-Containing Ester Approximately 271 grams of a trimethylolpropane based hydroxyl-containing ester was prepared as described in Example 3 were charged to a reactor equipped with a stirrer, thermometer, condenser and a caustic scrubber. Approximately 271 grams of a hydrocarbon diluent process oil was added along with 30 grams benzene solvent. The mixture was heated to 80° C. and 27 grams phosphorus pentasulfide was added over a period of one hour. The mixture was heated with agitation for 4 hours. The benzene solvent was removed by vacuum distillation and the partially phosphosulfurized hydroxyl-containing ester was filtered hot through paper to yield a clear amber fluid containing:
1.0% phosphorus
2.0% sulfur Approximately 200 grams of the above partially phosphosulfurized ester were reacted with 12 grams zinc oxide in the presence of 30 grams benzene and 3 grams 2-propanol solvents for 4 hours as 85°–95° C. The solvents were removed by vacuum distillation and the product was filtered through diatomaceous earth to yield a clear amber fluid.

EXAMPLE 5

Zinc Salt of Partially Phosphosulfurized Pentaerythritol Based Hydroxyl-Containing Ester Approximately 420 grams of a pentaerythritol based hydroxyl-containing ester prepared as described in Example 1 were charged to a reactor equipped with a stirrer, thermometer, condenser and a caustic scrubber. Approximately 420 grams of a hydrocarbon diluent process oil were added along with 30 grams benzene solvent. The mixture was heated to 80°–85° C. and 59 grams of phosphorus pentasulfide were added over a period of 1 hour. The reaction mixture was further held at 85° C. for a period of 4 additional hours at which point H$_2$S evolution diminished. The solvent was removed by vacuum distillation and the partially phosphosulfurized hydroxyl-containing ester was filtered hot through paper to remove unreacted phosphorus pentasulfide to yield a clear amber liquid.

Approximately 240 grams of the above phosphosulfurized ester was reacted with 24 grams of zinc oxide in the presence of 30 grams benzene and 3 grams 2-propanol as solvents for 4 hours at 80°–85° C. The solvents were removed by vacuum distillation to 100° C. The product was filtered through diatomaceous earth to yield a clear, amber fluid.

EXAMPLE 6

Pentaerythritol Based Hydroxyl-Containing Ester

This example illustrates the synthesis of a hydroxyl-containing ester. One mole of pentaerythritol and three moles of oleic acid were heated in the presence of a catalytic amount of p-toluene sulfonic acid (i.e., 0.1% of the combined weight of the reactants) at a temperature of up to 240° C. Water was simultaneously removed until water evolution stopped. The partial ester was filtered to yield a clear amber hydroxyl-containing ester fluid.

EXAMPLE 7

Zinc Salt of Partially Phosphosulfurized Pentaerythritol Based Hydroxyl-Containing Ester Approximately 465 grams of a pentaerythritol based hydroxyl-containing ester prepared as described in Example 6 were charged to a reactor equipped with a stirrer, thermometer, condenser and a caustic scrubber. Approximately 465 grams of a hydrocarbon diluent process oil were added along with 30 grams benzene solvent. The mixture was heated to about 90° C. and 28 grams of phosphorus pentasulfide were added over a period of ½ hour. The reaction mixture was further held at 90° C. for 4 additional hours at which point H$_2$S evolution diminished. The benzene solvent was removed by vacuum distillation and the partially phosphosulfurized hydroxyl-containing ester was filtered hot through paper to yield a clear amber liquid containing:
0.6% phosphorus
1.2% sulfur Approximately 200 grams of the above partially phosphosulfurized ester was reacted with 4.1 grams zinc oxide in the presence of 30 grams benzene and 3 grams 2-propanol solvents for 4 hours at 90°–95° C. The solvents were removed by vacuum distillation to 100° C. The product was filtered through diatomaceous earth to yield a clear amber fluid.

EXAMPLE 8

Zinc Salt of Partially Phosphosulfurized Trimethylolpropane Based Hydroxyl-Containing Ester Approximately 271 grams of a trimethylolpropane based hydroxyl-containing ester, prepared as described in Example 3, were charged to a reactor equipped with a stirrer, thermometer, condenser and a caustic scrubber. Approximately 271 grams of a hydrocarbon diluent process oil was added along with 30 grams of benzene solvent. The mixture was heated to 80° C. and 41 grams of phosphorus pentasulfide were added over a period of one hour. The mixture was heated at 90° C. with agitation for 4 hours. The benzene solvent was removed by vacuum distillation and the partially phosphosulfurized hydroxyl-containing ester was filtered hot through paper to yield a clear amber fluid containing:
1.7% phosphorus
3.3% sulfur Approximately 200 grams of the above partially phosphosulfurized ester were reacted with 16 grams zinc oxide, in the presence of 30 grams of benzene and 3 grams of 2-propanol as solvents, for 4 hours as 85°–95° C. The solvents were removed by vacuum distillation and the product was filtered through diatomaceous earth to yield a clear amber fluid.

The additives were blended into a fully formulated 5W20 automotive engine oil containing detergent/dispersant/inhibitor package and were tested for friction reducing properties using the Low Velocity Friction Apparatus.

LOW VELOCITY FRICTION APPARATUS (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (are a 0.08 in.²). Both surfaces were submerged in the test lubricant. Friction between the steel surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infintely variable-speed hydraulic transmission driven by a ½ HP electric motor. To vary the sliding speed, the output speed of the transmission is regulated by a lever cam-motor arrangement.

Procedure

The rubbing surfaces and 12–13 ml. of test lubricant are placed on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 6 to 8 microinches. The percentages by weight are percentages by weight of the total lubricating oil composition, including the usual additive package. The data are percent decrease in friction according to:

$$\frac{(U_k \text{ of oil alone}) - (U_k \text{ of Additive plus oil})}{(U_k \text{ of oil alone})} \times 100$$

Thus, the corresponding value for the oil alone would be zero for the form of the data used in Table 1 below.

TABLE 1

| | Friction Characteristics | | |
|---|---|---|---|
| | Additive Conc., | Reduction or % Change in Coefficient of Friction | |
| Example No. | Wt. % | 5 Ft./Min. | 30 Ft./Min. |
| Base Oil (Fully formulated engine oil) | — | 0 | 0 |
| Example 2 Zinc salt of partially phosphosulfurized pentaerythritol based hydroxyl-containing ester | 2<br>4 | 8<br>14 | 8<br>15 |
| Example 4 Zinc salt of partially phosphosulfurized trimethylolpropane based hydroxyl-containing ester | 4 | 7 | 8 |
| Example 5 Zinc salt of partially phosphosulfurized pentaerythritol based hydroxyl-containing ester | 4 | 9 | 17 |

These results clearly show the friction reducing properties of the phosphosulfurized hydroxyl-containing esters.

The examples were also tested for their antioxidation characteristics in the B-10 Catalytic Oxidation Test at 325° F. for 40 hours. Selected examples were dissolved in 200 second solvent paraffinic neutral lubricating oil to perform the antioxidation evaluation. The test lubricant composition is subjected to a stream of air which is bubbled through the composition at a rate of 5 liters per hour at 325° F. for 40 hours. Present in the composition comprising a 200 seconds paraffinic neutral oil in addition to the additive compound were metals commonly used as materials to construct engines namely:

(a) 15.6 sq. in. of sand-blasted iron wire;
(b) 0.78 sq. in. of polished copper wire;
(c) 0.87 sq. in. of polished aluminum wire; and
(d) 0.107 sq. in. of polished lead surface.

The test results are reported below in Table 2 and clearly show the antioxidation properties of the additives embodied herein.

TABLE 2

| | Catalytic Oxidation Test 40 Hours @ 325° F. | | | |
|---|---|---|---|---|
| | Additive Conc., Wt. % | Lead Loss, Mg | % Increase in Visc. of Oxidized Oil Using KV @ 210° F. | Neut. Number NN |
| Base Oil, 0% Additive 200" Solvent Paraffinic Neutral Lubricating Oil | — | 1.2 | 67 | 3.62 |
| Example 2 Zinc salt of partially phosphosulfurized pentaerythritol based hydroxyl-containing ester | 1<br>3 | 0.0<br>0.5 | 4<br>7 | 1.36<br>0.96 |
| Example 4 Zinc salt of partially phosphosulfurized trimethylolpropane based hydroxyl-containing ester | 1<br>3 | 0.0<br>0.0 | 8<br>5 | —<br>1.80 |
| Example 5 Zinc salt of partially phosphosulfurized pentaerythritol based hydroxyl-containing ester | 1<br>3 | 0.2<br>0.0 | 4<br>6 | 1.03<br>0.73 |
| Example 7 Zinc salt of partially phosphosulfurized pentaerythritol based hydroxyl-containing ester | 1<br>3 | 0.0<br>0.5 | 7<br>3 | 1.30<br>0.87 |
| Example 8 Zinc salt of partially phosphosulfurized trimethylolpropane based hydroxyl-containing ester | 1<br>3 | 0.0<br>0.0 | 9<br>6 | 1.91<br>2.58 |

The bearing corrosion inhibiting properties of exemplary compounds were tested via copper corrosivity tests, ASTM D 130-80 after dilution in 200 second solvent paraffinic neutral lubricating oil. The results are reported in Table 3 below.

TABLE 3

| | Copper Strip Corrosivity Characteristics | | |
|---|---|---|---|
| Example No. | Concentration in 200" SPN | ASTM D130-80 250° F., 3 Hrs. | ASTM D130-80 210° F., 6 Hrs |
| Example 2 Zinc salt of partially phosphosulfurized pentaerythritol based hydroxyl-containing ester | 1<br>3 | 1B<br>1B | 1B<br>1B |
| Example 4 Zinc salt of partially | 1 | 1B | 1A |

TABLE 3-continued

Copper Strip Corrosivity Characteristics

| Example No. | Concentration in 200″ SPN | ASTM D130-80 250° F., 3 Hrs. | ASTM D130-80 210° F., 6 Hrs |
|---|---|---|---|
| phosphosulfurized trimethylolpropane based hydroxyl-containing ester Example 5 | 3 | — | 1B |
| Zinc salt of partially phosphosulfurized pentaerythritol based hydroxyl-containing ester Example 7 | 1 3 | 1B 3B | 1B 1B |
| Zinc salt of partially phosphosulfurized pentaerythritol based hydroxyl-containing ester Example 8 | 1 3 | 1B 1B | 1B 1B |
| Zinc salt of partially phosphosulfurized trimethylolpropane based hydroxyl-containing ester | 1 | 1B | 1B |

As can be readily seen, the additive compounds of the present invention also possess good copper corrosivity characteristics and are clearly excellent multifunctional lubricant additives.

We claim:

1. A lubricant composition comprising a major proportion of an oil of lubricating viscosity or a grease or other solid lubricant prepared therefrom, and a friction reducing or antioxidant amount of a metal salt of a partially phosphosulfurized polyol based hydroxyl-containing ester, said ester being prepared by reacting a monocarboxylic acid having 4 to 30 carbon atoms with a polyol having the formula $$RC\{(CH_2)_xOH\}_3 \text{ or}$$
$$\{HO(CH_2)_x\}_3C(CH_2)_xO(CH_2)_xC\{(CH_2)_xOH\}_3$$

wherein R is hydrogen, a $(CH_2)_xOH$ group or a hydrocarbyl group, containing up to 8 carbon atoms and x is 1 to 4, the polyol having from about 5% to about 95% of its hydroxyls phosphosulfurized.

2. The composition of claim 1 wherein the ester is the iron, nickel, cobalt, molybdenum or zinc salt of partially phosphosulfurized polyols prepared from pentaerythritol or trimethylolalkane based hydroxyl-containing carboxylate esters.

3. The composition of claim 2 wherein the metal is zinc, derived from the group consisting of zinc oxide, zinc carbonate, zinc bicarbonate, zinc hydroxide and zinc chloride.

4. The composition of claim 3 wherein the metal salt is the zinc salt of a partially phosphosulfurized pentaerythritol based hydroxyl-containing carboxylate ester.

5. The composition of claim 3 wherein the ester is the trimethyolalkane based hydroxyl-containing carboxylate ester.

6. The composition of claim 1 wherein the oil of lubricating viscosity is selected from mineral oils, or fractions thereof, synthetic oils or mixtures of mineral and synthetic oils.

7. The composition of claim 1 wherein said oil is a mineral oil.

8. The composition of claim 1 wherein said oil is a synthetic oil.

9. The composition of claim 1 wherein said oil is a mixture of mineral and synthetic oils.

10. The composition of claim 1 wherein said major proportion is a grease.

11. A method of reducing fuel consumption in an internal combustion engine comprising treating the moving surfaces thereof with a lubricant composition as described in claim 1.

12. A product of reaction made by forming the metal salt of a partially phosphosulfurized polyol based hydroxyl-containing ester, said ester being prepared by reacting a monocarboxylic acid having 4 to 30 carbon atoms with a polyol having the formula $$RC[(CH_2)_xOH]_3 \text{ or}$$
$$[HO(CH_2)_x]_3C(CH_2)_xO(CH_2)_xC[(CH_2)_xOH]_3$$

wherein R is hydrogen, a $(CH_2)_xOH$ group or a hydrocarbyl group, containing up to 8 carbon atoms and x is 1 to 4, the polyol having from about 5% to about 95% of its hydroxyls phosphosulfurized.

13. The product of claim 12 wherein the metal in the metal salt is iron, nickel, cobalt, molybdenum or zinc and the hydroxyl-containing ester is derived from a pentaerythritol or a trimethylolalkane.

14. The product of claim 13 wherein the metal is zinc, derived from zinc oxide, zinc carbonate, zinc hydroxide or zinc chloride.

15. The product of claim 13 wherein the metal is zinc and the polyol is a pentaerythritol.

16. The product of claim 12 wherein the polyol is a trimethylolalkane.

17. The product of claim 12 wherein the polyol is pentaerythritol, the monocarboxylic acid is a mixture of 1.5 moles of oleic acid and 0.5 mole of pelargonic acid per mole of pentaerythritol and the metal is zinc.

18. The product of claim 12 wherein the polyol is trimethylolpropane, the monocarboxylic acid is a mixture of 1.5 moles of oleic acid and 0.5 mole pelargonic acid per mole of trimethylolpropane and the metal is zinc.

19. The product of claim 12 wherein the polyol is pentaerythritol, the monocarboxylic acid is 3 moles of oleic acid per mole of pentaerythritol and the metal is zinc.

* * * * *